United States Patent [19]

Greiner

[11] Patent Number: Plant 7,002

[45] Date of Patent: Aug. 29, 1989

[54] APPLE TREE NAMED PIONEER MAC

[75] Inventor: Ernest B. Greiner, Marlboro, N.Y.

[73] Assignee: Adams County Nursery, Inc., Aspers, Pa.

[21] Appl. No.: 225,075

[22] Filed: Jul. 20, 1988

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

A McIntosh type of apple tree discovered as a chance seedling in a cultivated area near Marlboro, N.Y., noted because of the resemblance of its fruit to the McIntosh but having more attractive, glassy, red skin, and the absence of speckling and russetting, later maturity and firmer fruit, the comparison being made to an unpatented variety known as the Rogers McIntosh growing in an orchard in which it was discovered.

1 Drawing Sheet

BACKGROUND OF THE INVENTION

The present invention is one which relates to a new and distinct variety of apple tree, which was discovered in a cultivated area as a chance seedling growing very close to the edge of the orchard in which the variety known as Rogers McIntosh is being grown, the differences making the seedling stand out and inviting its selection and for the reasons and distinctions hereinafter set forth.

The fruit of the tree hereof is of the high shouldered McIntosh type and has a very attractive skin with a red glassy appearance, lacking speckling or russetting, being a very hard type with the an outstandinly uniform shape for packing and packing out being better than the McIntosh with which it is compared.

It is noted that in observations where the comparison of the instant variety was made with adjacent trees of the Rogers McIntosh variety, the major difference was found to reside in the increased color and the firmer fruit.

I have chosen to call this particular variety "Pioneer Mac" as its commercial designation and have caused the same to be asexually reproduced by bud grafting.

I have found that the new variety is produced on a tree of medium size and medium vigor with an upright growth habit, and having leaves of small size, medium in length, and tapering to an abrupt point.

The fruit exhibits all the characteristics associated with McIntosh and particularly those which make it attractive.

The fruit is distinguished from some strains of McIntosh by its higher skin color, later maturity and firmness.

There is disclosed in the attached drawing some of the fruit which as will be noted disclosed very good color and glassy appearance, a detailed description of the tree and fruit following hereinafter.

DETAILED DESCRIPTION OF THE INVENTION

The following is a detailed description of the new variety and where color terminology has ordinary dictionary significance that is used and where it is significant, comparison with a color chart of known values being provided, specifically the Nickerson Color Fan produced by the Munsell Color Company, Baltimore, Md.

It should be noted that the colors and references thereto are made and disclosed in a drawing which is as nearly representative and true in color as it is possible to make the same in a photographic reproduction. The specimens described hereafter were grown at Marlboro, N.Y.

Tree: Medium, with a medium shoot extension, tall upright to vase-formed growth habit, slow growing, hardiness as good as standard McIntosh, with medium productivity.

*Trunk.*—Medium; smooth.

*Branches.*—Slender; much branching; moderate reddish brown (10R $\frac{3}{4}$) to dark reddish orange (10R 4/9); branches are covered with numerous medium lenticels.

*Leaves.*—Length approximately 88.8 mm; width at widest point averaging 57.2 mm; they are small but mediumly long becoming abruptly pointed; light green and smooth; overall shape is obliquely cordate.

*Margins.*—Crenate.

*Petiole.*—Short; slender; averaging 17.3 mm in dia.

Flowers:

*Date of first bloom.*—Approximately May 8–12.

*Date of full bloom.*—Approximately May 15–16.

*Time of flowering in relation to other cultivars.*—Blooms approximately 5–6 days before.

*Delicious: Bloom period is not different from other standard strains of McIntosh.*

Fruit:

*Maturity when eating ripe.*—September 10, approximately 7–10 days after Rogers McIntosh average firmness 15.0 lbs. 10.2% soluble solids and 4.5 starch rating (on a scale of 1, all starch to 5, no starch).

*Size.*—Uniform size averaging 74.0 mm in diameter and 59.7 mm in length.

*Shape.*—In longitudinal section, round-oblate. In cross-section, regular (round) to slightly angular.

*Stem.*—Medium to short; medium thick.

*Cavity.*—Accuminate to somewhat acute; medium depth and width, occasionally russetted.

*Basin.*—Shallow obtuse, somewhat furrowed.

*Skin.*—Thin; moderately tender; dark red (2.5 R 3/7) to moderate red (2.5 R 4/10); red coloration covering approximately 90 to 95% of the entire surface. No prominent lenticels.

*Calyx tube.*—Short; closed; stamens medium to basel.

*Core.*—Medium size; abaxile; ovules mostly open; core lines nearly meeting.

*Flesh.*—Juicy; white; crisp; slightly sub acid at harvest becoming sweet after storage, very good for desert purposes.

*Seeds.*—Number perfect 10; imperfect 0. Number in one locule 2. Length — Approximately 9.5 mm. Width — Approximately 4.5 mm. Form — Acute. Color — Brown.

Use: Fresh market; dessert; commercial market.

Keeping quality: Good; better than "Rogers" McIntosh after 145 days in storage.

Disease and Insect Resistance: About the same as the standard McIntosh.

I claim:

1. A new and distinct variety of apple tree, substantially as herein shown and described, characterized particularly as to novelty by its similarity to McIntosh, but having higher red skin color, glassy appearance, having no speckling or russetting, later maturity, firmer fruit, growing on a tree of medium size, of upright growth habit and having small size leaves, of medium length tapering to an abrupt point.

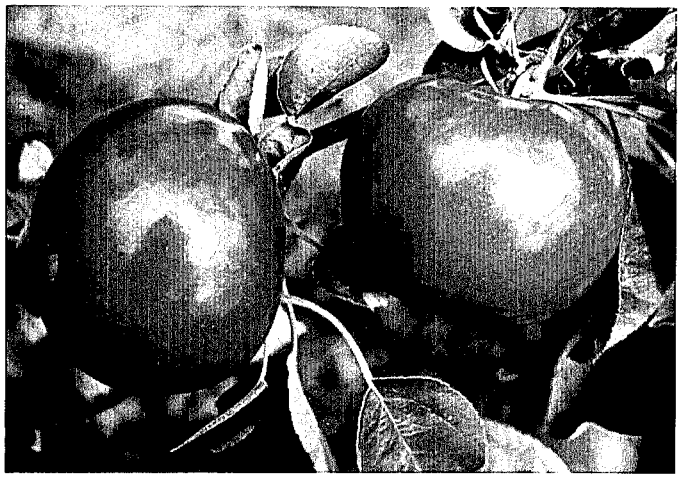

* * * * *